United States Patent
Inoue

(10) Patent No.: US 9,976,163 B2
(45) Date of Patent: May 22, 2018

(54) METHOD FOR PREVENTING REDUCTION OF POLYPEPTIDE BY ADDING AMINO ACID TO CULTURE SOLUTION

(71) Applicant: KYOWA HAKKO KIRIN CO., LTD., Tokyo (JP)

(72) Inventor: Hidetoshi Inoue, Tokyo (JP)

(73) Assignee: KYOWA HAKKO KIRIN CO., LTD, Tokyo (JP)

( * ) Notice: Subject to any disclaimer, the term of this patent is extended or adjusted under 35 U.S.C. 154(b) by 322 days.

(21) Appl. No.: 14/432,958

(22) PCT Filed: Oct. 3, 2013

(86) PCT No.: PCT/JP2013/076966
§ 371 (c)(1),
(2) Date: Apr. 1, 2015

(87) PCT Pub. No.: WO2014/054744
PCT Pub. Date: Apr. 10, 2014

(65) Prior Publication Data
US 2015/0275259 A1    Oct. 1, 2015

Related U.S. Application Data

(60) Provisional application No. 61/709,311, filed on Oct. 3, 2012.

(51) Int. Cl.
*C12P 21/00* (2006.01)
*C12P 21/02* (2006.01)
*C07K 16/00* (2006.01)

(52) U.S. Cl.
CPC .............. *C12P 21/00* (2013.01); *C07K 16/00* (2013.01); *C12P 21/02* (2013.01); *C07K 2317/14* (2013.01)

(58) Field of Classification Search
None
See application file for complete search history.

(56) References Cited

U.S. PATENT DOCUMENTS

| | | |
|---|---|---|
| 6,309,861 B1 | 10/2001 | Ambrosius et al. |
| 6,455,279 B1 | 9/2002 | Ambrosius et al. |
| 2003/0190316 A1 | 10/2003 | Kakuta et al. |
| 2005/0176109 A1 | 8/2005 | Yumioka et al. |
| 2009/0053786 A1 | 2/2009 | Kao et al. |
| 2011/0229933 A1 | 9/2011 | Krishnan et al. |
| 2012/0142901 A1 | 6/2012 | Yumioka et al. |
| 2012/0264918 A1 | 10/2012 | Yumioka et al. |
| 2013/0017598 A1 | 1/2013 | Kao et al. |
| 2013/0022625 A1 | 1/2013 | Igawa et al. |
| 2013/0102032 A1 | 4/2013 | Budach et al. |

FOREIGN PATENT DOCUMENTS

| | | |
|---|---|---|
| JP | 8-23995 A | 1/1996 |
| JP | 2850262 B2 | 1/1999 |
| JP | 2000-316591 A | 11/2000 |
| JP | 2001-61487 A | 3/2001 |
| JP | 2005-206602 A | 8/2005 |
| JP | 2010-533192 A | 10/2010 |
| JP | 2012-503487 A | 2/2012 |
| WO | 02/13860 A1 | 2/2002 |
| WO | 2009/009523 A2 | 1/2009 |
| WO | 2011/090088 A1 | 7/2011 |
| WO | 2011/134921 A1 | 11/2011 |

OTHER PUBLICATIONS

Search Report dated Dec. 17, 2013 issued in International Application No. PCT/JP2013/076966 (PCT/ISA/210).
Melody Trexler-Schmidt, et al; "Identification and Prevention of Antibody Disulfide Bond Reduction During Cell Culture Manufacturing"; Biotechnology and Bioengineering; Jun. 15, 2010; vol. 106; No. 3; pp. 452-461; 10 pgs total.
Bjorn K. Lyndersen, et al; "Acid Precipitation of Mammalian Cell Fermentation Broth"; Material and Methods; 1994; vol. 745; pp. 222-231; 10 pgs total.
Robert J. Falconer, et al; "Stabilization of a monoclonal antibody during purification and formulation by addiction of basic amino acid excipients"; Research Article; J Chem Technol Biotechnol; 2011; vol. 86; pp. 942-948; 7 pgs total.
Yung-Hsiang Kao, et al; "Mechanism of Antibody Reduction in Cell Culture Production Processes"; Biotechnology and Bioengineering; vol. 107; No. 4; Nov. 1, 2010; pp. 622-632; 11 pgs total.
Kristen L. Koterba, et al; "Thioredoxin 1 is responsible for antibody disulfide reduction in CHO cell culture"; Journal of Biotechnology; vol. 157; 2012; pp. 261-267.
Communication dated Feb. 17, 2016 issued by the European Patent Office in counterpart European Patent Application No. 13843339.6.
Paula Maria Lima e Castro; "Optimisation of CHO Cell Growth and Recombinant Interferon-y Production"; Department of Chemical & Biochemical Engineering University College London; XP002753385 & XP2753386; Sep. 29, 2008; pp. 1-228.
John G. Aunins, et al; "Induced Flocculation of Animal Cells in Suspension Culture"; Biotechnology and Bioengineering; vol. 34; XP002753387; Aug. 1, 1989; pp. 629-638.

*Primary Examiner* — Suzanne M Noakes
*Assistant Examiner* — Jae W Lee
(74) *Attorney, Agent, or Firm* — Sughrue Mion, PLLC

(57) ABSTRACT

The present invention provides a method for preventing the reduction of a desired polypeptide during purification in order to purify the polypeptide in high yield from a culture solution which contains recombinant host cells and the polypeptide.

10 Claims, No Drawings

METHOD FOR PREVENTING REDUCTION OF POLYPEPTIDE BY ADDING AMINO ACID TO CULTURE SOLUTION

TECHNICAL FIELD

The present invention relates to a method for preventing the reduction of a polypeptide expressed in recombinant host cells. The present invention also relates to a method for preventing the reduction of a polypeptide and efficiently purifying the polypeptide.

BACKGROUND ART

Due to the development of gene recombination technology, industrially useful polypeptides have been industrially produced. In particular, a lot of antibody pharmaceutical products and protein pharmaceutical products have been developed in the field of bio-pharmaceutical products.

Such an industrially useful polypeptide is often produced by culturing recombinant host cells transfected with a vector containing a gene encoding the polypeptide to be produced, and a technique for purifying the desired polypeptide from the culture solution is indispensable.

A typical step of purifying a polypeptide comprises a step of separating cells from a culture solution, and further comprises multiple steps in combination for removing cell fragments, unnecessary polypeptides, organic substances, inorganic substances or salts, and the like, in the culture solution from which the cells were removed.

In recent years, the cultivation technique has developed considerably, and therefore, in a culture solution, cells or cell fragments are present at a high density, and a polypeptide to be produced is present at a high density. As a result, in a step of separating the cells from the culture solution by utilizing a centrifuge or a membrane, a method for improving the efficiency, for example, the clogging of a membrane is reduced, or the like is demanded.

For example, a procedure called "acid precipitation", in which unnecessary substances in a culture solution are precipitated in advance by adding an acid to the culture solution when the cultivation is completed, is one of the methods of improving the efficiency of the step of separating cells from the culture solution immediately after the procedure (Non-Patent Document 1).

Further, the purification step should be capable of not only providing a polypeptide with a purity suitable for use, but also providing a high yield by preventing the denaturation or loss of the polypeptide during purification. Further, the purification step is desirably configured to comprise steps in an efficient order so as to make use of the effect of the respective steps.

Typical denaturation of a polypeptide during purification includes the reduction of a disulfide bond of a polypeptide, the cleavage of a peptide bond, the association of polypeptides, and the like before or after removing cells from the culture solution. It is known that in particular, a thioredoxin system is involved in the reduction of a disulfide bond of a polypeptide in some cases (Non-Patent Documents 2, 3, and 4).

This thioredoxin system is essentially intracellularly present in the host cells which produce a polypeptide. However, in the production of a polypeptide, during cultivation of recombinant host cells, due to apoptosis or the like of the cells, after cultivation of the recombinant host cells, cell membranes of the recombinant host cells are ruptured by mechanical stimulation through each procedure of the purification step, and therefore, thioredoxin, thioredoxin reductase, glucose-6-phosphate dehydrogenase, a hexokinase, and substrates therefor, which are the constituent elements of the thioredoxin system, are released in the culture solution.

Therefore, it is considered that in the production of a polypeptide, the thioredoxin system is also present in the culture solution, and this can be a cause of the reduction of a polypeptide to be produced.

Examples of a conventional method for preventing the reduction of a disulfide bond in which this thioredoxin system is involved include a method of adding aurothioglucose (ATG) which is a thioredoxin inhibitor or ethylenediaminetetraacetic acid (EDTA) which inhibits a hexokinase to a culture solution after culturing recombinant host cells and before separating the cells or after separating the cells.

Additional examples thereof include a method of depleting glucose-6-phosphate (G6P) or reduced nicotinamide adenine dinucleotide phosphate (NADPH) by filling with air in the culture solution after recombinant host cells are cultured and the cells are separated, and the like (Patent Document 1).

RELATED ART DOCUMENTS

Patent Documents

Patent Document 1: WO 2009/009523

Non-Patent Documents

Non-Patent Document 1: Lydersen B. K., Brehm-Gibson T., Murel A., 1994, Annals New York Academy of Sciences, 745, 222-31

Non-Patent Document 2: Trexler-Schmidt M., Sargis S., Chiu J., Sze-Khoo S., Mun M., Kao Y. H., Laird M. W., 2010, Identification and prevention of antibody disulfide bond reduction during cell culture manufacturing, Biotechnol. Bioeng., 106, 452-461

Non-Patent Document 3: Kao Y. H., Hewitt D. P., Trexler-Schmidt M., Laird M. W., 2010. Mechanism of antibody reduction in cell culture production processes, Biotechnol. Bioeng., 107, 622-632

Non-Patent Document 4: Koterba K. L., Borgschulte T., Laird M. W., 2012. Thioredoxin 1 is responsible for antibody disulfide reduction in CHO cell culture, J. Biotechnol., 157, 261-267

SUMMARY OF THE INVENTION

Problems to be Solved by the Invention

Among the conventional methods of preventing the reduction of a polypeptide during purification, a method of adding a compound which inhibits the activity of the constituent elements of the thioredoxin system to a culture solution needed a purification step of removing the compound later as a compound harmful to human bodies.

Depending on the purification step, such a compound cannot be sufficiently removed in some cases, and therefore this method has a problem in versatility. Further, the method of depleting the constituent elements of the thioredoxin system by filling with air needs special equipment, and therefore is not suitable for industrial application.

An object of the present invention is to provide a method for preventing the reduction of a polypeptide during purification in order to purify a desired polypeptide in high yield from a culture solution which contains recombinant host cells and the polypeptide without using a compound harmful to human bodies or without using special equipment.

Another object of the present invention is to provide a method for preventing the reduction of a polypeptide during purification and efficiently purifying the polypeptide.

Means for Solving the Problems

The present invention relates to the following (1) to (13).
(1) A method for preventing the reduction of a polypeptide expressed in recombinant host cells and secreted in a culture solution, comprising adding an amino acid to the culture solution.
(2) The method described in (1), wherein the method comprises a step of removing the recombinant host cells from the culture solution, and the amino acid is added to the culture solution before this step.
(3) The method described in (1), wherein the method comprises a step of removing the recombinant host cells from the culture solution, and the amino acid is added to the culture solution after this step is started.
(4) The method described in (2) or (3), wherein the method comprises a flocculation step before the step of removing the recombinant host cells from the culture solution.
(5) The method described in (4), wherein at least acid precipitation is used in the flocculation step.
(6) The method described in (5), wherein the amino acid is added to the culture solution after the acid precipitation.
(7) The method described in any one of (1) to (6), wherein the amino acid is arginine, lysine, or histidine.
(8) The method described in (6) or (7), wherein the amino acid is added to the culture solution so that the final concentration of the amino acid is from 0.05 mol/L to 1 mol/L.
(9) The method described in any one of (6) to (8), wherein the amino acid is added to the culture solution so that the final concentration of the amino acid is 0.5 mol/L.
(10) The method described in any one of (6) to (8), wherein the amino acid is added to the culture solution so that the final concentration of the amino acid is 0.1 mol/L.
(11) The method described in any one of (1) to (10), wherein the polypeptide is an antibody or an antibody fragment.
(12) The method described in any one of (1) to (11), wherein the recombinant host cells are Chinese hamster ovary (CHO) cells.
(13) A method for purifying a polypeptide using the method described in any one of (1) to (12).

Effects of the Invention

According to the present invention, the reduction of a polypeptide during purification can be easily prevented by adding an amino acid to a culture solution without using a compound harmful to human bodies or without using special equipment, and a desired polypeptide can be purified in high yield.

EMBODIMENTS FOR CARRYING OUT THE INVENTION

The host cells to be used for the recombinant host cells in the present invention are not particularly limited and may be any cells such as eukaryotic cells (such as animal cells, plant cells, and yeast cells), prokaryotic cells (such as *Escherichia coli* and *Bacillus subtilis*), and the like.

Specific examples thereof include eukaryotic host cells. Preferred examples thereof include Chinese hamster ovary (CHO) cells, mouse myeloma cells (NS0 and SP2/0), rat myeloma cells (IR983F), Syrian hamster kidney-derived BHK cells, human myeloma cells (Namalwa), embryonic stem cells, and fertilized egg cells.

The recombinant host cells in the present invention are transformed cells into which a gene encoding a polypeptide to be produced has been integrated. The transformed cells can be obtained by introducing a vector containing a gene encoding a polypeptide to be produced into a cell line.

The medium to be used for the culture solution in the present invention may be any as long as it is a medium suitable for culturing each of the recombinant host cells. Specific examples thereof include a serum-containing medium, a medium containing no animal-derived component such as serum albumin or a serum fraction, a serum-free medium, a protein-free medium, and the like. Preferred examples thereof include a serum-free medium and a protein-free medium.

More specific examples thereof include RPMI1640 medium, Dulbecco's modified MEM (DMEM) medium, F12 medium, Iscove's Modified Dulbecco's (IMDM) medium, EX-CELL302 medium, CD-CHO medium, IS CD-CHO medium, and the like.

To the culture solution, a physiologically active substance, a nutrient factor, or the like essential for the growth of each of the recombinant host cells can be added as needed. As the addition method, any method may be employed, for example, such a substance or a factor is added to a medium in advance before cultivation, or such a substance or a factor is added appropriately thereto as a supplementary medium or a supplementary solution during cultivation.

The culture solution in the present invention includes not only a culture solution before culturing the recombinant host cells, but also a culture solution containing the recombinant host cells after culturing the recombinant host cells, and a culture supernatant obtained by removing the recombinant host cells (sometimes also referred to as eluate or the like).

The polypeptide in the present invention is not particularly limited as long as it is an industrially useful protein, and examples thereof include a protein to be used as a pharmaceutical product.

Examples of the protein include antibodies, erythropoietin, darbepoetin, thrombopoietin, tissue-type plasminogen activators, pro-urokinase, thrombomodulin, antithrombin III, protein C, blood coagulation factor VII, blood coagulation factor VIII, blood coagulation factor IX, blood coagulation factor X, blood coagulation factor XI, blood coagulation factor XII, prothrombin complexes, fibrinogen, albumin, gonadotropic hormones, thyroid-stimulating hormones, epidermal growth factors (EGF), hepatocyte growth factors (HGF), keratinocyte growth factors, activin, bone morphogenetic factors, G-CSF, M-CSF, SCF, interferon (IFN)-α, IFN-β, IFN-γ, interleukin (IL)-2, IL-6, IL-10, IL-11, soluble IL-4 receptors, tumor necrosis factor-α, Dnase 1, galactosidase, α-glucosidase, glucocerebrosidase, hemoglobin, transferrin, partial fragments thereof, and the like.

Additional examples of the protein include a protein obtained by binding a different protein or a partial fragment or the like of a different protein to the above-described protein or a partial fragment thereof chemically or through genetic engineering (hereinafter referred to as "binding protein").

Examples of the partial fragment of the protein include a polypeptide, in which one or more amino acids are deleted in the amino acid sequence of the original protein, and which has the function of the original protein. Examples of the method of obtaining such a polypeptide having an amino acid sequence in which one or more amino acids are deleted in the amino acid sequence include a method of introducing a site-specific mutation into a gene encoding a polypeptide having the amino acid sequence of the original protein using a site-specific mutagenesis method [Molecular Cloning, A Laboratory Manual, Second Edition, Cold Spring Harbor Laboratory Press (1989), Current Protocols in Molecular Biology, John Wiley & Sons (1987-1997), Nucleic Acids Research, 10, 6487 (1982), Proc. Natl. Acad. Sci. USA, 79, 6409 (1982), Gene, 34, 315 (1985), or Proc. Natl. Acad. Sci. USA, 82, 488 (1985)] or the like.

Examples of the different protein include different types of proteins from the target protein among the above-described proteins and the like. Further, examples of the partial fragment of the different protein include a polypeptide, in which one or more amino acids are deleted in the amino acid sequence of the original protein, and which has the function of the original protein in the same manner as the above-described partial fragment of the protein.

Examples of the method of binding two different types of proteins or partial fragments thereof include a method in which cDNAs encoding the respective proteins or partial fragments are ligated to each other, thereby constructing a DNA encoding a binding protein, and the DNA is inserted into a vector, and the vector is introduced into host cells to express the binding protein.

Examples of the antibody include not only monoclonal antibodies derived from animals such as humans, mice, rats, hamsters, rabbits, monkeys, goats, cattle, camels, and alpacas, but also human chimeric antibodies, humanized antibodies, human antibodies, antibody fragments thereof, and the like. Further, the immunoglobulin class of the antibody is not particularly limited, and may be any class such as IgG (such as IgG1, IgG2, IgG3, or IgG4), IgA, IgD, IgE, or IgM. When the antibody is used as a pharmaceutical product, IgG or IgM is preferred.

Examples of the human chimeric antibody include an antibody composed of a heavy chain variable region (hereinafter referred to as "VH") and a light chain variable region (hereinafter referred to as "VL") of a non-human animal antibody, and a heavy chain constant region (hereinafter referred to as "CH") and a light chain constant region (hereinafter referred to as "CL") of a human antibody.

The human chimeric antibody of the present invention can be produced by obtaining cDNAs encoding the VH and VL, respectively, and inserting the obtained cDNAs respectively into an expression vector for animal cells having genes encoding the CH and CL, respectively, of a human antibody, thereby constructing a human chimeric antibody expression vector, and then, introducing the expression vector into host cells to express the human chimeric antibody.

The CH of the human chimeric antibody may be any as long as it belongs to the human immunoglobulin (hereinafter referred to as "hIg"), however, preferably, a CH belonging to the hIgG class is used. Further, any one of the subclasses belonging to the hIgG class such as hIgG1, hIgG2, hIgG3, and hIgG4 can be used. The CL of the human chimeric antibody may be any as long as it belongs to the hIg, and a CL belonging to the κ class or the λ class can be used.

The humanized antibody is also sometimes called "human CDR-grafted antibody", and is referred to as an antibody in which amino acid sequences of complementarity determining regions (hereinafter referred to as "CDRs") of the VH and VL of a non-human animal antibody are grafted into appropriate positions of the VH and VL of a human antibody.

The human CDR-grafted antibody of the present invention can be produced by constructing cDNAs encoding variable (V) regions in which the amino acid sequences of CDRs of the VH and VL of a non-human animal antibody are grafted into frameworks (hereinafter referred to as "FR") of the VH and VL of any human antibody, and inserting the constructed cDNAs respectively into an expression vector for animal cells having genes encoding the CH and CL, respectively, of a human antibody, thereby constructing a human CDR-grafted antibody expression vector, and then, introducing the expression vector into host cells to express the human CDR-grafted antibody.

The CH of the humanized antibody may be any as long as it belongs to the hIg, however, preferably, a CH belonging to the hIgG class is used. Further, any one of the subclasses belonging to the hIgG class such as hIgG1, hIgG2, hIgG3, and hIgG4 can be used. The CL of the humanized antibody may be any as long as it belongs to the hIg, and a CL belonging to the κ class or the λ class can be used.

The human antibody originally refers to an antibody naturally existing in the human body, but also includes an antibody obtained from a human antibody phage library or a human antibody-producing transgenic animal, which is produced based on the recent advance in genetic engineering, cell engineering, and developmental engineering techniques, and the like.

The antibody naturally existing in the human body can be produced by, for example isolating human peripheral blood lymphocytes, immortalizing the lymphocytes by infection with EB virus or the like, cloning the lymphocytes to isolate a DNA encoding the antibody, inserting the DNA into an expression vector for animal cells, thereby constructing a human antibody expression vector, and then, introducing the expression vector into host cells to express the antibody.

The human antibody phage library is a library in which an antibody fragment such as a Fab or a single-chain antibody (scFv) is expressed on the phage surface by inserting an antibody gene prepared from human B cells into a phage gene.

A phage which expresses an antibody fragment having a desired antigen-binding activity on its surface can be recovered from the library by using the binding activity to a substrate having an antigen immobilized thereon as an index. The antibody fragment can be further converted into a human antibody molecule composed of two complete H chains and two complete L chains by a genetic engineering technique.

The human antibody-producing transgenic animal means an animal in which a human antibody gene is integrated into cells. Specifically, for example, a human antibody-producing transgenic mouse can be produced by introducing a human antibody gene into mouse ES cells, and grafting the ES cells into an early embryo of a mouse, and then developing the embryo.

The human antibody from the human antibody-producing transgenic animal can be produced by obtaining a human antibody-producing hybridoma using a conventional hybridoma preparation method carried out in non-human animals to isolate a DNA encoding the antibody, inserting the DNA into an expression vector for animal cells, thereby constructing a human antibody expression vector, and then, introducing the expression vector into host cells to express the human antibody.

Examples of the antibody fragment include Fab, F(ab')$_2$, Fab', scFv, a dimerized V region (diabody), a disulfide stabilized V region (dsFv), a peptide containing a CDR, and the like.

The Fab is an antibody fragment, which is obtained by binding about a half of the H chain on the N-terminal side and the full L chain to each other through a disulfide bond among the fragments obtained by treatment of IgG with papain which is a protease (cleavage of the H chain at the amino acid residue at position 224), has a molecular weight of about 50,000, and has an antigen-binding activity.

The Fab of the present invention can be obtained by treating the antibody of the present invention with papain. Further, the Fab can also be produced by inserting a DNA encoding the Fab of the antibody into an expression vector for prokaryote or an expression vector for eukaryote, and introducing the expression vector into a prokaryote or a eukaryote to express the Fab.

The F(ab')$_2$ is a fragment, which is composed of two Fab regions obtained by degradation of IgG downstream of the disulfide bond in a hinge region with pepsin which is a protease, and bound to each other at the hinge region, has a molecular weight of about 100,000, and has an antigen-binding activity. The F(ab')$_2$ of the present invention can be obtained by treating the antibody of the present invention with pepsin. Further, the F(ab')$_2$ can also be produced by binding the following Fab' fragments through a thioether bond or a disulfide bond.

The Fab' is an antibody fragment, which is obtained by cleaving the disulfide bond in the hinge region of the above-described F(ab')$_2$, has a molecular weight of about 50,000, and has an antigen-binding activity. The Fab' of the present invention can be obtained by treating the F(ab')$_2$ of the present invention with a reducing agent such as dithiothreitol.

Further, the Fab' can also be produced by inserting a DNA encoding the Fab' fragment of the antibody into an expression vector for prokaryote or an expression vector for eukaryote, and introducing the expression vector into a prokaryote or a eukaryote to express the Fab'.

The scFv is an antibody fragment, which is obtained by linking one VH and one VL using an appropriate peptide linker (hereinafter referred to as "P"), which is a VH-P-VL or VL-P-VH polypeptide, and which has an antigen-binding activity.

The scFv of the present invention can be produced by obtaining cDNAs encoding the VH and VL, respectively, of the monoclonal antibody of the present invention, constructing a DNA encoding the scFv, inserting the DNA into an expression vector for prokaryote or an expression vector for eukaryote, and introducing the expression vector into a prokaryote or a eukaryote to express the scFv.

The diabody is an antibody fragment which is obtained by dimerizing scFv and has a divalent antigen-binding activity. The divalent antigen-binding activities can be the same or one of them can be used as a different antigen binding activity.

The diabody of the present invention can be produced by obtaining cDNAs encoding the VH and VL, respectively, of the antibody of the present invention, constructing a DNA encoding scFv such that the length of the amino acid sequence of a peptide linker is 8 residues or less, inserting the DNA into an expression vector for prokaryote or an expression vector for eukaryote, and introducing the expression vector into a prokaryote or a eukaryote to express the scFv.

The dsFv is an antibody fragment obtained by binding polypeptides, in which one amino acid residue of each of the VH and VL is substituted with a cysteine residue, through a disulfide bond between the cysteine residues. The amino acid residue to be substituted with a cysteine residue can be selected based on the prediction of the tertiary structure of an antibody according to a known method (Protein Engineering, 7, 697, 1994). The dsFv of the present invention can be produced by obtaining cDNAs encoding the VH and VL, respectively, of the antibody of the present invention, constructing a DNA encoding the dsFv, inserting the DNA into an expression vector for prokaryote or an expression vector for eukaryote, and introducing the expression vector into a prokaryote or a eukaryote to express the dsFv.

A peptide containing a CDR is composed of at least one or more regions of the CDRs of the VH or VL. The peptides containing multiple CDRs can be bound directly or through an appropriate peptide linker.

The peptide containing a CDR of the present invention can be produced by constructing a DNA encoding a CDR of the VH or VL of the antibody of the present invention, inserting the DNA into an expression vector for prokaryote or an expression vector for eukaryote, and introducing the expression vector into a prokaryote or a eukaryote to express the peptide.

The reduction of a polypeptide in the present invention includes the reduction of a disulfide bond contained in a polypeptide to be produced. Therefore, when the polypeptide to be produced does not contain a disulfide bond, the present invention is not applied.

The reduction of a disulfide bond includes the reduction caused by various factors and conditions of the production process, and also includes the reduction caused by various reducing agents. Specifically, for example, the reduction caused by a thioredoxin system present in a culture solution in the production process of a polypeptide to be produced is included.

The thioredoxin system includes a hydrogen donor system for the reduction of a disulfide bond in a polypeptide, which includes thioredoxin, thioredoxin reductase, and NADPH. The thioredoxin exists in an oxidized form having a disulfide bond at the active site and in a reduced form having a free thiol group at the active site.

The reduced thioredoxin reduces and cleaves an intramolecular or intermolecular disulfide bond of a substrate protein by converting itself into the oxidized form. The thioredoxin converted into the oxidized form is reduced by reduced thioredoxin reductase and returns to reduced thioredoxin again. The thioredoxin reductase converted into the oxidized form is reduced by NADPH and returns to reduced thioredoxin reductase again.

NADPH is generated from, for example, oxidized nicotinamide adenine dinucleotide phosphate (NADP+) and glucose-6-phosphate by glucose-6-phosphate dehydrogenase. Glucose-6-phosphate is generated from glucose and adenosine triphosphate (ATP) by a hexokinase.

Examples of the amino acid to be used in the present invention include alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine. Further, additional examples thereof include amino acids which do not constitute proteins such as ornithine and creatine, and also include unnatural amino acids.

From the viewpoint of effectively preventing the reduction of a polypeptide, the amino acid to be used in the present invention is preferably a basic amino acid, and more preferably arginine, histidine, or lysine.

The form of the amino acid to be used in the present invention may be any form as long as it exists as an amino acid in an aqueous solution, and examples thereof include an amino acid, a salt, a hydrate, and a mixture containing the same.

The arginine to be used in the present invention may be any of arginine, a salt, a hydrate, and a mixture containing the same as long as it exists as arginine in an aqueous solution. Specific examples thereof include compounds represented by CAS Registry Number: 74-79-3, CAS Registry Number: 1119-34-2, CAS Registry Number: 4320-30-3, CAS Registry Number: 157-06-2, CAS Registry Number: 627-75-8, CAS Registry Number: 26982-20-7, CAS Registry Number: 7200-25-1, CAS Registry Number: 32042-43-6, and the like. Preferred examples thereof include a compound represented by CAS Registry Number: 1119-34-2.

The lysine to be used in the present invention may be any of lysine, a salt, a hydrate, and a mixture containing the same as long as it exists as lysine in an aqueous solution. Specific examples thereof include compounds represented by CAS Registry Number: 56-87-1, CAS Registry Number: 657-27-2, CAS Registry Number: 657-26-1, CAS Registry Number: 70-54-2, CAS Registry Number: 70-53-1, CAS Registry Number: 617-68-5, CAS Registry Number: 923-27-3, CAS Registry Number: 7274-88-6, and the like. Preferred examples thereof include a compound represented by CAS Registry Number: 657-27-2.

The histidine to be used in the present invention may be any of histidine, a salt, a hydrate, and a mixture containing the same as long as it exists as histidine in an aqueous solution. Specific examples thereof include compounds represented by CAS Registry Number: 71-00-1, CAS Registry Number: 645-35-2, CAS Registry Number: 6027-02-7, CAS Registry Number: 5934-29-2, CAS Registry Number: 7048-02-4, CAS Registry Number: 351-50-8, CAS Registry Number: 6341-24-8, CAS Registry Number: 15474-90-5, CAS Registry Number: 4998-57-6, CAS Registry Number: 123333-71-1, and the like. Preferred examples thereof include a compound represented by CAS Registry Number: 5934-29-2.

Examples of the method of adding an amino acid to a culture solution in the present invention include a method of directly adding an amino acid in the solid form to a culture solution and a method of adding an aqueous amino acid solution to a culture solution. From the viewpoint of effectively preventing the reduction of a polypeptide, an amino acid is added to a culture solution preferably such that the final concentration thereof is between 0.05 mol/L and 1 mol/L, more preferably such that the final concentration thereof is 0.5 mol/L or 0.1 mol/L.

The final concentration thereof can be appropriately set in accordance with the properties of the desired polypeptide, or the properties of the cell line selected as the host cells. The temperature at which the amino acid is added may be any temperature, but is preferably from 4° C. to 40° C., more preferably from 10° C. to 25° C. The temperature can be appropriately set in accordance with the properties of the desired polypeptide, or the properties of the cell line selected as the host cells.

The incubation time after adding the amino acid to the culture solution may be 0 hours, and also may be several hours to several days. The incubation time can be appropriately set in accordance with the properties of the desired polypeptide, or the properties of the cell line selected as the host cells.

The method of the present invention can comprise a step of removing the recombinant host cells from the culture solution. Specific examples of the step of removing the recombinant host cells from the culture solution include a centrifugal separation step, a cross-flow filtration step (a tangential flow filtration step), a filtration step using a depth filter, a filtration step using a surface filter, a filtration step using a membrane filter, an ultrafiltration step, a salting-out step, a dialysis step, and a step using these methods in combination.

Preferred examples of the step of removing the recombinant host cells from the culture solution in the present invention include a step of transferring the culture solution in a culture vessel to a continuous centrifuge and filtering the obtained culture supernatant. After the step of removing the recombinant host cells from the culture solution in the present invention, a chromatography step, a concentration step, or the like is included.

The type of chromatography to be used in the chromatography step may be any as long as it is a method known to those skilled in the art such as column chromatography or membrane chromatography. For affinity chromatography among the chromatographic techniques, Protein A chromatography, Protein G chromatography, or the like is used.

Examples of the type of chromatography other than the affinity chromatography include ion exchange chromatography, hydrophobic chromatography, gel filtration chromatography, reverse-phase chromatography, adsorption chromatography, multimodal chromatography, and the like.

In the present invention, the addition of an amino acid before the step of removing the recombinant host cells from the culture solution specifically includes, for example, the addition of an amino acid to a culture solution containing the recombinant host cells during cultivation or after completion of cultivation.

The addition of an amino acid after the step of removing the recombinant host cells from the culture solution in the present invention is started includes, for example, the addition of an amino acid to a culture solution by the time before the chromatography step is started and after the step to be performed for the purpose of removing the recombinant host cells from the culture solution is started, preferably includes the addition of an amino acid to a culture solution after all the steps of removing the recombinant host cells from the culture solution are completed and before the chromatography step is started.

Incidentally, before the step of removing the recombinant host cells from the culture solution in the present invention, a flocculation step can be included. In the present invention, the flocculation refers to a method in which unnecessary substances in the culture solution are aggregated and precipitated by adding a substance called "flocculant" to the culture solution containing the recombinant host cells during cultivation or after completion of cultivation.

Preferred examples of the flocculant include acids, alkalis, salts, chitosan, caprylic acid, charged polymers, ammonium sulfate, polymer electrolytes, and the like. In the case where the flocculation step is included, the time point when the amino acid is added may be before, during, or after the flocculation.

The flocculation step includes, for example, acid precipitation. The acid precipitation includes a step of adjusting the pH of the culture solution to be acidic by adding an acid as the flocculant to the culture solution containing the recombinant host cells after culturing the recombinant host cells among the flocculation procedures known to those skilled in the art.

The acid to be added to the culture solution for the purpose of performing the acid precipitation may be any as long as the acid can be removed in the subsequent purification step. Specific examples thereof include citric acid, acetic acid, and the like, and preferred examples thereof include citric acid.

In the case where the acid precipitation is included before the step of removing the recombinant host cells in the present invention, the time point when the amino acid is added to the culture solution may be before, during, or after the acid precipitation. The time point is preferably after the acid precipitation is performed and before the step of removing the recombinant host cells, or after the acid precipitation is performed and the step of removing the recombinant host cells is started and before the chromatography step is started.

By adding the amino acid to the culture solution after acid precipitation is performed, both of an effect of aggregation and precipitation of unnecessary substances in the culture solution by acid precipitation and an effect of prevention of the reduction of a polypeptide by the addition of the amino acid to the culture solution are achieved, and therefore, the polypeptide secreted in the culture solution can be efficiently purified.

In the present invention, examples of the method of adding an acid to the culture solution for the purpose of performing the acid precipitation include a method of directly adding an acid in the solid form and a method of adding an aqueous acid solution. The acid concentration in the aqueous acid solution may be any, but can be set to, for example, 1 mol/L or the like. The pH of the culture solution after the acid is added is preferably from 3.5 to 6.0, more preferably 4.5 to 5.5.

EXAMPLES

Example 1

Example of Method for Preventing Reduction of Polypeptide by Adding Arginine to Culture Solution Containing Cells and Polypeptide By culturing recombinant host cells obtained using CHO-K1 cells as host cells, a cell culture solution containing the recombinant host cells and an IgG1 antibody secreted from the cells at a concentration of about 2 to 3 g/L was prepared.

To this culture solution, an aqueous solution of 2 mol/L arginine hydrochloride (manufactured by Ajinomoto Co., Inc.) (hereinafter "2 mol/L aqueous arginine hydrochloride solution") was added, whereby culture solutions containing arginine at a final concentration of 0.1 mol/L or 0.5 mol/L were prepared. Further, as a control, a culture solution to which water was added in place of the 2 mol/L aqueous arginine hydrochloride solution was also prepared.

Each of the culture solutions was divided and placed in two vessels, and the cells contained in one of the vessels were all homogenized using a homogenizer. The culture solution in which the cells were homogenized and the culture solution in which the cells were not homogenized were mixed at 4:6. These mixed culture solutions containing arginine at 0.5, 0.1, or 0 (control) mol/L were centrifuged at 6410×g for 15 minutes to precipitate the cells, large cell fragments, and the like, and the supernatants were recovered. Further, by filtering each supernatant using Stericup-GP (Product No. SCGPU02RE, manufactured by Millipore, Inc.), an eluate from which small cell fragments were removed was obtained.

To each of thus obtained eluates, an aqueous solution of 1 mol/L anhydrous citric acid (Product No. 26046-2001, manufactured by Junsei Chemical Co., Ltd.) (hereinafter "1 mol/L aqueous citric acid solution") or an aqueous solution of 3 mol/L Tris (trishydroxyaminomethane Product No. 40326-09, manufactured by Kanto Chemical Co., Inc.) (hereinafter "3 mol/L aqueous Tris solution") was added to adjust the pH to 7.0.

Each eluate was placed in a bottle capable of aeration and stirred with a stirrer while continuously filling with nitrogen gas in the upper surface of the liquid at room temperature, whereby dissolved oxygen in the eluate was decreased. From each eluate, a 0.04-mL aliquot was sampled at 12, 24, 36, and 48 hours after adjusting the pH to 7.0.

Thus obtained test subjects replicated the state in which after arginine was added to the culture solution, the recombinant host cells or the cell fragments were removed from the culture solution, and the resulting solution was left at room temperature until it was subjected to the chromatography step in the actual purification step.

The respective test subjects sampled were analyzed by SDS-PAGE. As a result, in the case of the test subject of the control, significant reduction of the antibody was observed in all the samples. On the other hand, in the case of the test subject containing arginine at a final concentration of 0.1 mol/L, the reduction of the antibody was observed in the samples taken out at 24 hours and thereafter from the start of filling with nitrogen gas, but the degree thereof was minor compared to the case of the control.

Further, in the case of the test subject containing arginine at a final concentration of 0.5 mol/L, the reduction of the antibody was not observed even in the sample taken out at 48 hours from the start of filling with nitrogen gas. These results showed that by adding arginine to the culture solution, the reduction of a polypeptide secreted in the culture solution from the recombinant host cells could be prevented.

Example 2

Example of Method for Preventing Reduction of Polypeptide by Adding Arginine to Culture Supernatant By culturing recombinant host cells obtained using CHO-K1 cells as host cells, a cell culture solution containing the recombinant host cells and an IgG1 antibody secreted from the cells at a concentration of about 2 to 3 g/L was prepared.

This culture solution was divided and placed in two vessels, and the cells contained in one of the vessels were all homogenized using a homogenizer. The culture solution in which the cells were homogenized and the culture solution in which the cells were not homogenized were mixed at 4:6.

This mixed culture solution was centrifuged at 6410×g for 15 minutes to precipitate the cells, large cell fragments, and the like, and the supernatant was recovered. Further, by filtering the supernatant using Stericup-GP (Product No. SCGPU02RE, manufactured by Millipore, Inc.), an eluate from which small cell fragments were removed was obtained.

To thus obtained eluate, a 2 mol/L aqueous arginine hydrochloride solution was added, whereby culture solutions containing arginine at a final concentration of 0.1 mol/L or 0.5 mol/L were prepared. Further, as a control, a culture solution to which water was added in place of the 2 mol/L aqueous arginine hydrochloride solution was also prepared.

To each of the eluates to which arginine was added and the control, a 1 mol/L aqueous citric acid solution or a 3 mol/L aqueous Tris solution was added to adjust the pH to 7.0.

Each eluate was placed in a bottle capable of aeration and stirred with a stirrer while continuously filling with nitrogen gas in the upper surface of the liquid at room temperature, whereby dissolved oxygen in the eluate was decreased.

From each eluate, a 0.04-mL aliquot was sampled at 12, 24, 36, and 48 hours after adjusting the pH to 7.0. Thus obtained test subjects replicated the state in which after the recombinant host cells or the cell fragments were removed from the culture solution, arginine was added thereto, and the resulting solution was left at room temperature until it was subjected to the chromatography step in the actual purification step.

The respective test subjects sampled were analyzed by SDS-PAGE. As a result, in the case of the test subject of the control, significant reduction of the antibody was observed in all the samples. On the other hand, in the case of the test subject containing arginine at a final concentration of 0.1 mol/L, the reduction of the antibody was observed in the samples taken out at 24 hours and thereafter from the start of filling with nitrogen gas, but the degree thereof was minor compared to the case of the control.

Further, in the case of the test subject containing arginine at a final concentration of 0.5 mol/L, the reduction of the antibody was not observed even in the sample taken out at 48 hours from the start of filling with nitrogen gas. These results showed that by adding arginine to the culture supernatant, the reduction of a polypeptide secreted in the culture solution from the recombinant host cells could be prevented.

Example 3

Example of Method for Preventing Reduction of Polypeptide by Adding Arginine to Culture Solution Containing Recombinant Host Cells and Polypeptide After Performing Acid Precipitation By culturing recombinant host cells obtained using CHO-K1 cells as host cells, a cell culture solution containing the recombinant host cells and an IgG1 antibody secreted from the cells at a concentration of about 2 to 3 g/L was prepared. To this culture solution, a 1 mol/L aqueous citric acid solution or a 3 mol/L aqueous Tris solution was added to adjust the pH to 5.1, whereby acid precipitation was performed.

To the culture solution after performing acid precipitation, a 2 mol/L aqueous arginine hydrochloride solution was added, whereby a culture solution containing arginine at a final concentration of 0.1 mol/L was prepared. Further, as a control, a culture solution to which water was added in place of the 2 mol/L aqueous arginine hydrochloride solution was also prepared.

Each of the culture solutions was divided and placed in two vessels, and the cells contained in one of the vessels were all homogenized using a homogenizer. The culture solution in which the cells were homogenized and the culture solution in which the cells were not homogenized were mixed at 4:6.

These mixed culture solutions containing arginine at 0.1, or 0 (control) mol/L were centrifuged at 6410×g for 15 minutes to precipitate the cells, large cell fragments, and the like, and the supernatants were recovered. Further, by filtering each supernatant using Stericup-GP (Product No. SCGPU02RE, manufactured by Millipore, Inc.), an eluate from which small cell fragments were removed was obtained.

Each of thus obtained eluates was placed in a bottle capable of aeration and stirred with a stirrer while continuously filling with nitrogen gas in the upper surface of the liquid at room temperature, whereby dissolved oxygen in the eluate was decreased. The filling with nitrogen gas was continued from the time point when the pH was adjusted to 5.1 until 6 hours thereafter. By adding a 1 mol/L aqueous citric acid solution or a 3 mol/L aqueous Tris solution to each eluate after the filling with nitrogen gas was completed, the pH was adjusted to 6.0.

Each eluate was placed in a bottle capable of aeration and stirred with a stirrer while continuously filling with nitrogen gas in the upper surface of the liquid at room temperature, whereby dissolved oxygen in the eluate was decreased. From each eluate, a 0.04-mL aliquot was sampled at 18, 30, and 42 hours after adjusting the pH to 6.0.

Thus obtained test subjects replicated the state in which after acid precipitation was performed, arginine was added to the culture solution, and further the recombinant host cells or the cell fragments were removed from the culture solution, and then, the pH was adjusted to 6.0, and the resulting solution was left at room temperature until it was subjected to the chromatography step in the actual purification step.

The respective test subjects sampled were analyzed by SDS-PAGE. As a result, in the case of the test subject of the control, the reduction of the antibody was observed in the samples taken out at 18 hours and thereafter from the adjustment of the pH to 6.0. On the other hand, in the case of the test subject containing arginine at a final concentration of 0.1 mol/L, the reduction of the antibody was not observed in all the samples.

These results showed that by adding arginine to the culture solution after performing acid precipitation and before the step of removing the recombinant host cells from the culture solution, the reduction of a polypeptide secreted in the culture solution from the cells could be prevented.

Example 4

Example of Method for Preventing Reduction of Polypeptide by Adding Arginine to Culture Supernatant After Performing Acid Precipitation By culturing recombinant host cells obtained using CHO-K1 cells as host cells, a cell culture solution containing the recombinant host cells and an IgG1 antibody secreted from the cells at a concentration of about 2 to 3 g/L was prepared. To this culture solution, a 1 mol/L aqueous citric acid solution or a 3 mol/L aqueous Tris solution was added to adjust the pH to 5.1, whereby acid precipitation was performed.

The culture solution after performing acid precipitation was divided and placed in two vessels, and the cells contained in one of the vessels were all homogenized using a homogenizer. The culture solution in which the cells were homogenized and the culture solution in which the cells were not homogenized were mixed at 4:6.

This mixed culture solution was centrifuged at 6410×g for 15 minutes to precipitate the cells, large cell fragments, and the like, and the culture supernatant was recovered. Further, by filtering the supernatant using Stericup-GP (Product No. SCGPU02RE, manufactured by Millipore, Inc.), an eluate from which small cell fragments were removed was obtained.

Thus obtained eluate was placed in a bottle capable of aeration and stirred with a stirrer while continuously filling with nitrogen gas in the upper surface of the liquid at room temperature, whereby dissolved oxygen in the eluate was decreased. The filling with nitrogen gas was continued from the time point when the pH was adjusted to 5.1 until 6 hours thereafter.

A 2 mol/L aqueous arginine hydrochloride solution was added to the eluate after the filling with nitrogen gas was completed, whereby an eluate containing arginine at a final concentration of 0.1 mol/L was prepared. Further, by adding a 1 mol/L aqueous citric acid solution or a 3 mol/L aqueous Tris solution thereto, the pH was adjusted to 6.0.

Further, as a control, an eluate to which water was added in place of the 2 mol/L aqueous arginine hydrochloride solution was also prepared. Also to this control, a 1 mol/L aqueous citric acid solution or a 3 mol/L aqueous Tris solution was added, whereby the pH was adjusted to 6.0. Each eluate was placed in a bottle capable of aeration and stirred with a stirrer while continuously filling with nitrogen gas in the upper surface of the liquid at room temperature, whereby dissolved oxygen in the eluate was decreased.

From each eluate, a 0.04-mL aliquot was sampled at 18, 30, and 42 hours after adjusting the pH to 6.0. Thus obtained test subjects replicated the state in which after acid precipitation was performed, the recombinant host cells or the cell fragments were removed from the culture solution, and further arginine was added thereto, and then, the pH was adjusted to 6.0, and the resulting solution was left at room temperature until it was subjected to the chromatography step in the actual purification step.

The respective test subjects sampled were analyzed by SDS-PAGE. As a result, in the case of the test subject of the control, the reduction of the antibody was observed in the samples taken out at 18 hours and thereafter from the adjustment of the pH to 6.0. On the other hand, in the case of the test subject containing arginine at a final concentration of 0.1 mol/L, the reduction of the antibody was not observed in all the samples.

These results showed that by adding arginine to the culture solution after acid precipitation was performed and the step of removing the recombinant host cells from the culture solution was started, the reduction of a polypeptide secreted in the culture solution from the cells could be prevented.

Example 5

Effect of Order of Addition of Arginine on Membrane Filterability in Cell Separation Step By culturing recombinant host cells obtained using CHO-K1 cells as host cells, a cell culture solution containing the recombinant host cells and an IgG1 antibody secreted from the cells at a concentration of about 2 to 3 g/L was prepared.

This cell culture solution was called "Culture Solution A". To the Culture Solution A, a 2 mol/L aqueous arginine hydrochloride solution was added, whereby a culture solution containing arginine at a final concentration of 0.1 mol/L was prepared and called "Culture Solution B". To the Culture Solution B, a 1 mol/L aqueous citric acid solution or a 3 mol/L aqueous Tris solution was added to adjust the pH to 5.1, and the resulting solution was called "Culture Solution C".

To the Culture Solution A, a 1 mol/L aqueous citric acid solution or a 3 mol/L aqueous Tris solution was added to adjust the pH to 5.1, and the resulting solution was called "Culture Solution D". To the Culture Solution D, a 2 mol/L aqueous arginine hydrochloride solution was added, whereby a culture solution containing arginine at a final concentration of 0.1 mol/L was prepared and called "Culture Solution E". Each of thus prepared culture solutions was centrifuged at 2090×g for 10 minutes to precipitate the cells, large cell fragments, and the like, and the culture supernatant was recovered.

Subsequently, by filtering each of the culture supernatants using Millex-GP (Product No. SLGP033RS, manufactured by Millipore, Inc.), the membrane filterability of the respective culture supernatants was evaluated. Incidentally, this membrane filterability replicates the membrane filterability in the cell separation step. As a result, the culture supernatants derived from the Culture Solutions A, B, C, D, and E caused clogging of the membrane at the time when being filtered through the membrane in an amount of about 8.8 mL, 8.3 mL, 16.8 mL, 33.7 mL, and 33.1 mL, respectively.

Based on the results of the Culture Solutions A and B, it was revealed that the membrane filterability in the cell separation step was not decreased by the addition of arginine to the culture solution. Further, based on the results of the Culture Solutions D and E, it was revealed that the membrane filterability in the cell separation step was not decreased by the addition of arginine to the culture solution after performing acid precipitation.

Still further, based on the results of the Culture Solutions B, C, and E, it was revealed that the membrane filterability in the cell separation step was improved by the addition of arginine to the culture solution either before or after performing acid precipitation as compared with the case where acid precipitation was not performed. However, it was revealed that the addition of arginine to the culture solution may be performed before performing acid precipitation, but more preferably, it is performed after performing acid precipitation.

Example 6

Example of Method for Preventing Reduction of Polypeptide by Adding Lysine to Culture Solution Containing Recombinant Host Cells and Polypeptide By culturing recombinant host cells obtained using CHO-K1 cells as host cells, a cell culture solution containing the recombinant host cells and an IgG1 antibody secreted from the cells at a concentration of about 2 to 3 g/L was prepared. To this culture solution, an aqueous solution of 2 mol/L lysine hydrochloride (Product No. 123-01461, manufactured by Wako Pure Chemical Industries Ltd.) (hereinafter "2 mol/L aqueous lysine hydrochloride solution") was added, whereby culture solutions containing lysine at a final concentration of 0.1 mol/L or 0.5 mol/L were prepared.

Each of the culture solutions was divided and placed in two vessels, and the cells contained in one of the vessels were all homogenized using a homogenizer. The culture solution in which the cells were homogenized and the culture solution in which the cells were not homogenized were mixed at 4:6.

These mixed culture solutions containing lysine at 0.1, or 0.5 mol/L were centrifuged at 6410×g for 15 minutes to precipitate the cells, large cell fragments, and the like, and the supernatants were recovered. Further, by filtering each supernatant using Stericup-GP (Product No. SCGPU02RE, manufactured by Millipore, Inc.), an eluate from which small cell fragments were removed was obtained.

To each of thus obtained eluates, a 1 mol/L aqueous citric acid solution or a 3 mol/L aqueous Tris solution was added to adjust the pH to 7.0. Each eluate was placed in a bottle capable of aeration and stirred with a stirrer while continuously filling with nitrogen gas in the upper surface of the liquid at room temperature, whereby dissolved oxygen in the eluate was decreased.

From each eluate, a 0.04-mL aliquot was sampled at 12, 24, 36, and 48 hours after adjusting the pH to 7.0. Thus obtained test subjects replicated the state in which after lysine was added to the culture solution, the recombinant host cells or the cell fragments were removed from the culture solution, and the resulting solution was left at room temperature until it was subjected to the chromatography step in the actual purification step.

The respective test subjects sampled were analyzed by SDS-PAGE. As a result, in the case of the test subject containing lysine at a final concentration of 0.1 mol/L, the reduction of the antibody was observed in the samples taken out at 24 hours and thereafter from the start of filling with nitrogen gas.

On the other hand, in the case of the control in Example 1, the reduction of the antibody was observed in the samples taken out at 12 hours and thereafter from the start of filling with nitrogen gas. Further, in the case of the test subject containing lysine at a final concentration of 0.5 mol/L, the reduction of the antibody was not observed even in the sample taken out at 48 hours from the start of filling with nitrogen gas.

These results showed that by adding lysine to the culture solution, the reduction of a polypeptide secreted in the culture solution from the recombinant host cells could be prevented.

Example 7

Example of Method for Preventing Reduction of Polypeptide by Adding Histidine to Culture Solution Containing Recombinant Host Cells and Polypeptide By culturing recombinant host cells obtained using CHO-K1 cells as host cells, a cell culture solution containing the recombinant host cells and an IgG1 antibody secreted from the cells at a concentration of about 2 to 3 g/L was prepared.

To this culture solution, an aqueous solution of 0.75 mol/L histidine hydrochloride monohydrate (Product No. 088-00705, manufactured by Wako Pure Chemical Industries Ltd.) (hereinafter "0.75 mol/L aqueous histidine hydrochloride solution") was added, whereby a culture solution containing histidine at a final concentration of 0.1 mol/L was prepared.

This culture solution was divided and placed in two vessels, and the cells contained in one of the vessels were all homogenized using a homogenizer. The culture solution in which the cells were homogenized and the culture solution in which the cells were not homogenized were mixed at 4:6. This mixed culture solution containing histidine at 0.1 mol/L was centrifuged at 6410×g for 15 minutes to precipitate the cells, large cell fragments, and the like, and the supernatant was recovered. Further, by filtering the supernatant using Stericup-GP (Product No. SCGPU02RE, manufactured by Millipore, Inc.), an eluate from which small cell fragments were removed was obtained.

To thus obtained eluate, a 1 mol/L aqueous citric acid solution or a 3 mol/L aqueous Tris solution was added to adjust the pH to 7.0. The eluate was placed in a bottle capable of aeration and stirred with a stirrer while continuously filling with nitrogen gas in the upper surface of the liquid at room temperature, whereby dissolved oxygen in the eluate was decreased.

From the eluate, a 0.04-mL aliquot was sampled at 12, 24, 36, and 48 hours after adjusting the pH to 7.0. Thus obtained test subject replicated the state in which after histidine was added to the culture solution, the recombinant host cells or the cell fragments were removed from the culture solution, and the resulting solution was left at room temperature until it was subjected to the chromatography step in the actual purification step.

The respective test subjects sampled were analyzed by SDS-PAGE. As a result, in the case of the test subject containing histidine at a final concentration of 0.1 mol/L, the reduction of the antibody was observed in the samples taken out at 24 hours and thereafter from the start of filling with nitrogen gas.

On the other hand, in the case of the control in Example 1, the reduction of the antibody was observed in the samples taken out at 12 hours and thereafter from the start of filling with nitrogen gas. These results showed that by adding histidine to the culture solution, the reduction of a polypeptide secreted in the culture solution from the recombinant host cells could be prevented.

Example 8

Example of Method for Preventing Reduction of Polypeptide by Adding Lysine to Culture Supernatant By culturing recombinant host cells obtained using CHO-K1 cells as host cells, a cell culture solution containing the recombinant host cells and an IgG1 antibody secreted from the cells at a concentration of about 2 to 3 g/L was prepared.

This culture solution was divided and placed in two vessels, and the cells contained in one of the vessels were all homogenized using a homogenizer. The culture solution in which the cells were homogenized and the culture solution in which the cells were not homogenized were mixed at 4:6. This mixed culture solution was centrifuged at 6410×g for 15 minutes to precipitate the cells, large cell fragments, and the like, and the supernatant was recovered. Further, by filtering the supernatant using Stericup-GP (Product No. SCGPU02RE, manufactured by Millipore, Inc.), an eluate from which small cell fragments were removed was obtained.

To thus obtained eluate, a 2 mol/L aqueous lysine hydrochloride solution was added, whereby culture solutions containing lysine at a final concentration of 0.1 mol/L or 0.5 mol/L were prepared.

To each of the eluates to which lysine was added, a 1 mol/L aqueous citric acid solution or a 3 mol/L aqueous Tris solution was added to adjust the pH to 7.0. Each eluate was placed in a bottle capable of aeration and stirred with a stirrer while continuously filling with nitrogen gas in the upper surface of the liquid at room temperature, whereby dissolved oxygen in the eluate was decreased.

From each eluate, a 0.04-mL aliquot was sampled at 12, 24, 36, and 48 hours after adjusting the pH to 7.0. Thus obtained test subjects replicated the state in which after the recombinant host cells or the cell fragments were removed from the culture solution, lysine was added thereto, and the resulting solution was left at room temperature until it was subjected to the chromatography step in the actual purification step.

The respective test subjects sampled were analyzed by SDS-PAGE. As a result, in the case of the test subject containing lysine at a final concentration of 0.1 mol/L, the reduction of the antibody was observed in the samples taken out at 24 hours and thereafter from the start of filling with nitrogen gas.

On the other hand, in the case of the control in Example 2, the reduction of the antibody was observed in the samples taken out at 12 hours and thereafter from the start of filling with nitrogen gas. Further, in the case of the test subject containing lysine at a final concentration of 0.5 mol/L, the reduction of the antibody was not observed even in the sample taken out at 48 hours from the start of filling with nitrogen gas. These results showed that by adding lysine to the culture supernatant, the reduction of a polypeptide secreted in the culture solution from the recombinant host cells could be prevented.

Example 9

Example of Method for Preventing Reduction of Polypeptide by Adding Histidine to Culture Supernatant By culturing recombinant host cells obtained using CHO-K1 cells as host cells, a cell culture solution containing the recombinant host cells and an IgG1 antibody secreted from the cells at a concentration of about 2 to 3 g/L was prepared.

This culture solution was divided and placed in two vessels, and the cells contained in one of the vessels were all homogenized using a homogenizer. The culture solution in which the cells were homogenized and the culture solution in which the cells were not homogenized were mixed at 4:6.

This mixed culture solution was centrifuged at 6410×g for 15 minutes to precipitate the cells, large cell fragments, and the like, and the supernatant was recovered. Further, by filtering the supernatant using Stericup-GP (Product No. SCGPU02RE, manufactured by Millipore, Inc.), an eluate from which small cell fragments were removed was obtained.

To thus obtained eluate, a 0.75 mol/L aqueous histidine hydrochloride solution was added, whereby a culture solution containing histidine at a final concentration of 0.1 mol/L was prepared. To the eluate to which histidine was added, a 1 mol/L aqueous citric acid solution or a 3 mol/L aqueous Tris solution was added to adjust the pH to 7.0.

The eluate was placed in a bottle capable of aeration and stirred with a stirrer while continuously filling with nitrogen gas in the upper surface of the liquid at room temperature, whereby dissolved oxygen in the eluate was decreased. From the eluate, a 0.04-mL aliquot was sampled at 12, 24, 36, and 48 hours after adjusting the pH to 7.0.

Thus obtained test subjects replicated the state in which after the recombinant host cells or the cell fragments were removed from the culture solution, histidine was added thereto, and the resulting solution was left at room temperature until it was subjected to the chromatography step in the actual purification step.

The respective test subjects sampled were analyzed by SDS-PAGE. As a result, in the case of the test subject containing histidine at a final concentration of 0.1 mol/L, the reduction of the antibody was observed in the samples taken out at 24 hours and thereafter from the start of filling with nitrogen gas.

On the other hand, in the case of the control in Example 2, the reduction of the antibody was observed in the samples taken out at 12 hours and thereafter from the start of filling with nitrogen gas. These results showed that by adding histidine to the culture supernatant, the reduction of a polypeptide secreted in the culture solution from the recombinant host cells could be prevented.

Example 10

Example of Method for Preventing Reduction of Polypeptide by Adding Lysine to Culture Solution Containing Recombinant Host Cells and Polypeptide After Performing Acid Precipitation By culturing recombinant host cells obtained using CHO-K1 cells as host cells, a cell culture solution containing the recombinant host cells and an IgG1 antibody secreted from the cells at a concentration of about 2 to 3 g/L was prepared. To this culture solution, a 1 mol/L aqueous citric acid solution or a 3 mol/L aqueous Tris solution was added to adjust the pH to 5.1, whereby acid precipitation was performed.

To the culture solution after performing acid precipitation, a 2 mol/L aqueous lysine hydrochloride solution was added, whereby a culture solution containing lysine at a final concentration of 0.1 mol/L was prepared.

This culture solution was divided and placed in two vessels, and the cells contained in one of the vessels were all homogenized using a homogenizer. The culture solution in which the cells were homogenized and the culture solution in which the cells were not homogenized were mixed at 4:6.

This mixed culture solution containing lysine at 0.1 mol/L was centrifuged at 6410×g for 15 minutes to precipitate the cells, large cell fragments, and the like, and the supernatant was recovered. Further, by filtering the supernatant using Stericup-GP (Product No. SCGPU02RE, manufactured by Millipore, Inc.), an eluate from which small cell fragments were removed was obtained.

Thus obtained eluate was placed in a bottle capable of aeration and stirred with a stirrer while continuously filling with nitrogen gas in the upper surface of the liquid at room temperature, whereby dissolved oxygen in the eluate was decreased. The filling with nitrogen gas was continued from the time point when the pH was adjusted to 5.1 until 6 hours thereafter.

To the eluate after the filling with nitrogen gas was completed, a 1 mol/L aqueous citric acid solution or a 3 mol/L aqueous Tris solution was added, whereby the pH was adjusted to 6.0. The eluate was placed in a bottle capable of aeration and stirred with a stirrer while continuously filling with nitrogen gas in the upper surface of the liquid at room temperature, whereby dissolved oxygen in the eluate was decreased. From the eluate, a 0.04-mL aliquot was sampled at 18, 30, and 42 hours after adjusting the pH to 6.0.

Thus obtained test subject replicated the state in which after acid precipitation was performed, lysine was added to the culture solution, and further the recombinant host cells or the cell fragments were removed from the culture solution, and then, the pH was adjusted to 6.0, and the resulting solution was left at room temperature until it was subjected to the chromatography step in the actual purification step.

The respective test subjects sampled were analyzed by SDS-PAGE. As a result, in the case of the test subject containing lysine at a final concentration of 0.1 mol/L, the reduction of the antibody was observed in the samples taken out at 30 hours and thereafter from the adjustment of the pH to 6.0.

On the other hand, in the case of the test subject of the control in Example 3, the reduction of the antibody was observed in the samples taken out at 18 hours and thereafter from the adjustment of the pH to 6.0. These results showed that by adding lysine to the culture solution after performing acid precipitation and before the step of removing the recombinant host cells from the culture solution, the reduction of a polypeptide secreted in the culture solution from the recombinant host cells could be prevented.

Example 11

Example of Method for Preventing Reduction of Polypeptide by Adding Histidine to Culture Solution Containing Recombinant Host Cells and Polypeptide After Performing Acid Precipitation By culturing recombinant host cells obtained using CHO-K1 cells as host cells, a cell culture solution containing the recombinant host cells and an IgG1 antibody secreted from the cells at a concentration of about 2 to 3 g/L was prepared. To this culture solution, a 1 mol/L aqueous citric acid solution or a 3 mol/L aqueous Tris solution was added to adjust the pH to 5.1, whereby acid precipitation was performed.

To the culture solution after performing acid precipitation, a 0.75 mol/L aqueous histidine hydrochloride solution was added, whereby a culture solution containing histidine at a final concentration of 0.1 mol/L was prepared.

This culture solution was divided and placed in two vessels, and the cells contained in one of the vessels were all homogenized using a homogenizer. The culture solution in which the cells were homogenized and the culture solution in which the cells were not homogenized were mixed at 4:6.

This mixed culture solution containing histidine at 0.1 mol/L was centrifuged at 6410×g for 15 minutes to precipitate the cells, large cell fragments, and the like, and the supernatant was recovered. Further, by filtering the supernatant using Stericup-GP (Product No. SCGPU02RE, manufactured by Millipore, Inc.), an eluate from which small cell fragments were removed was obtained.

Thus obtained eluate was placed in a bottle capable of aeration and stirred with a stirrer while continuously filling with nitrogen gas in the upper surface of the liquid at room temperature, whereby dissolved oxygen in the eluate was decreased. The filling with nitrogen gas was continued from the time point when the pH was adjusted to 5.1 until 6 hours thereafter.

To the eluate after the filling with nitrogen gas was completed, a 1 mol/L aqueous citric acid solution or a 3 mol/L aqueous Tris solution was added, whereby the pH was adjusted to 6.0. The eluate was placed in a bottle capable of aeration and stirred with a stirrer while continuously filling with nitrogen gas in the upper surface of the liquid at room temperature, whereby dissolved oxygen in the eluate was decreased.

From the eluate, a 0.04-mL aliquot was sampled at 18, 30, and 42 hours after adjusting the pH to 6.0. Thus obtained test subject replicated the state in which after acid precipitation was performed, histidine was added to the culture solution, and further the recombinant host cells or the cell fragments were removed from the culture solution, and then, the pH was adjusted to 6.0, and the resulting solution was left at room temperature until it was subjected to the chromatography step in the actual purification step.

The respective test subjects sampled were analyzed by SDS-PAGE. As a result, in the case of the test subject containing histidine at a final concentration of 0.1 mol/L, the reduction of the antibody was not observed in all the samples. On the other hand, in the case of the test subject of the control in Example 3, the reduction of the antibody was observed in the samples taken out at 18 hours and thereafter from the adjustment of the pH to 6.0.

These results showed that by adding histidine to the culture solution after performing acid precipitation and before the step of removing the recombinant host cells from the culture solution, the reduction of a polypeptide secreted in the culture solution from the recombinant host cells could be prevented.

Example 12

Example of Method for Preventing Reduction of Polypeptide by Adding Lysine to Culture Supernatant After Performing Acid Precipitation By culturing recombinant host cells obtained using CHO-K1 cells as host cells, a cell culture solution containing the recombinant host cells and an IgG1 antibody secreted from the cells at a concentration of about 2 to 3 g/L was prepared. To this culture solution, a 1 mol/L aqueous citric acid solution or a 3 mol/L aqueous Tris solution was added to adjust the pH to 5.1, whereby acid precipitation was performed.

The culture solution after performing acid precipitation was divided and placed in two vessels, and the cells contained in one of the vessels were all homogenized using a homogenizer. The culture solution in which the cells were homogenized and the culture solution in which the cells were not homogenized were mixed at 4:6.

This mixed culture solution was centrifuged at 6410×g for 15 minutes to precipitate the cells, large cell fragments, and the like, and the culture supernatant was recovered. Further, by filtering the supernatant using Stericup-GP (Product No. SCGPU02RE, manufactured by Millipore, Inc.), an eluate from which small cell fragments were removed was obtained.

Thus obtained eluate was placed in a bottle capable of aeration and stirred with a stirrer while continuously filling with nitrogen gas in the upper surface of the liquid at room temperature, whereby dissolved oxygen in the eluate was decreased. The filling with nitrogen gas was continued from the time point when the pH was adjusted to 5.1 until 6 hours thereafter.

A 2 mol/L aqueous lysine hydrochloride solution was added to the eluate after the filling with nitrogen gas was completed, whereby an eluate containing lysine at a final concentration of 0.1 mol/L was prepared. Further, by adding a 1 mol/L aqueous citric acid solution or a 3 mol/L aqueous Tris solution thereto, the pH was adjusted to 6.0.

The eluate was placed in a bottle capable of aeration and stirred with a stirrer while continuously filling with nitrogen gas in the upper surface of the liquid at room temperature, whereby dissolved oxygen in the eluate was decreased. From the eluate, a 0.04-mL aliquot was sampled at 18, 30, and 42 hours after adjusting the pH to 6.0.

Thus obtained test subjects replicated the state in which after acid precipitation was performed, the recombinant host cells or the cell fragments were removed from the culture solution, and further lysine was added thereto, and then, the pH was adjusted to 6.0, and the resulting solution was left at room temperature until it was subjected to the chromatography step in the actual purification step.

The respective test subjects sampled were analyzed by SDS-PAGE. As a result, in the case of the test subject containing lysine at a final concentration of 0.1 mol/L, the reduction of the antibody was observed in the samples taken out at 30 hours and thereafter from the adjustment of the pH to 6.0.

On the other hand, in the case of the test subject of the control in Example 4, the reduction of the antibody was observed in the samples taken out at 18 hours and thereafter from the adjustment of the pH to 6.0. These results showed that by adding lysine to the culture solution after acid precipitation was performed and the step of removing the recombinant host cells from the culture solution was started, the reduction of a polypeptide secreted in the culture solution from the cells could be prevented.

Example 13

Example of Method for Preventing Reduction of Polypeptide by Adding Histidine to Culture Supernatant After Performing Acid Precipitation By culturing recombinant host cells obtained using CHO-K1 cells as host cells, a cell culture solution containing the recombinant host cells and an IgG1 antibody secreted from the cells at a concentration of about 2 to 3 g/L was prepared. To this culture solution, a 1 mol/L aqueous citric acid solution or a 3 mol/L aqueous Tris solution was added to adjust the pH to 5.1, whereby acid precipitation was performed.

The culture solution after performing acid precipitation was divided and placed in two vessels, and the cells contained in one of the vessels were all homogenized using a homogenizer. The culture solution in which the cells were homogenized and the culture solution in which the cells were not homogenized were mixed at 4:6.

This mixed culture solution was centrifuged at 6410×g for 15 minutes to precipitate the cells, large cell fragments, and the like, and the culture supernatant was recovered. Further, by filtering the supernatant using Stericup-GP (Product No. SCGPU02RE, manufactured by Millipore, Inc.), an eluate from which small cell fragments were removed was obtained.

Thus obtained eluate was placed in a bottle capable of aeration and stirred with a stirrer while continuously filling with nitrogen gas in the upper surface of the liquid at room temperature, whereby dissolved oxygen in the eluate was decreased. The filling with nitrogen gas was continued from the time point when the pH was adjusted to 5.1 until 6 hours thereafter.

A 0.75 mol/L aqueous histidine hydrochloride solution was added to the eluate after the filling with nitrogen gas was completed, whereby an eluate containing histidine at a final concentration of 0.1 mol/L was prepared. Further, by adding a 1 mol/L aqueous citric acid solution or a 3 mol/L aqueous Tris solution thereto, the pH was adjusted to 6.0.

The eluate was placed in a bottle capable of aeration and stirred with a stirrer while continuously filling with nitrogen gas in the upper surface of the liquid at room temperature, whereby dissolved oxygen in the eluate was decreased. From the eluate, a 0.04-mL aliquot was sampled at 18, 30, and 42 hours after adjusting the pH to 6.0.

Thus obtained test subjects replicated the state in which after acid precipitation was performed, the recombinant host cells or the cell fragments were removed from the culture solution, and further histidine was added thereto, and then, the pH was adjusted to 6.0, and the resulting solution was left at room temperature until it was subjected to the chromatography step in the actual purification step.

The respective test subjects sampled were analyzed by SDS-PAGE. As a result, in the case of the test subject containing histidine at a final concentration of 0.1 mol/L, the reduction of the antibody was not observed in all the samples.

On the other hand, in the case of the test subject of the control in Example 4, the reduction of the antibody was observed in the samples taken out at 18 hours and thereafter from the adjustment of the pH to 6.0. These results showed that by adding histidine to the culture solution after acid precipitation was performed and the step of removing the recombinant host cells from the culture solution was started, the reduction of a polypeptide secreted in the culture solution from the cells could be prevented.

Example 14

Effect of Order of Addition of Arginine, Lysine, or Histidine on Membrane Filterability in Cell Separation Step By culturing recombinant host cells obtained using CHO-K1 cells as host cells, a cell culture solution containing the recombinant host cells and an IgG1 antibody secreted from the cells at a concentration of about 2 to 3 g/L was prepared.

This culture solution was called "Culture Solution A". To the Culture Solution A, a 2 mol/L aqueous arginine hydrochloride solution was added, whereby a culture solution containing arginine at a final concentration of 0.1 mol/L was prepared and called "Culture Solution B". To the Culture Solution A, a 2 mol/L aqueous lysine hydrochloride solution was added, whereby a culture solution containing lysine at a final concentration of 0.1 mol/L was prepared and called "Culture Solution C".

To the Culture Solution A, a 0.75 mol/L aqueous histidine hydrochloride solution was added, whereby a culture solution containing histidine at a final concentration of 0.1 mol/L was prepared and called "Culture Solution D". To the Culture Solution B, a 1 mol/L aqueous citric acid solution or a 3 mol/L aqueous Tris solution was further added to adjust the pH to 5.1, and the resulting solution was called "Culture Solution E".

To the Culture Solution C, a 1 mol/L aqueous citric acid solution or a 3 mol/L aqueous Tris solution was further added to adjust the pH to 5.1, and the resulting solution was called "Culture Solution F". To the Culture Solution D, a 1 mol/L aqueous citric acid solution or a 3 mol/L aqueous Tris solution was further added to adjust the pH to 5.1, and the resulting solution was called "Culture Solution G".

To the Culture Solution A, a 1 mol/L aqueous citric acid solution or a 3 mol/L aqueous Tris solution was added to adjust the pH to 5.1, and the resulting solution was called "Culture Solution H". To the Culture Solution H, a 2 mol/L aqueous arginine hydrochloride solution was further added, whereby a culture solution containing arginine at a final concentration of 0.1 mol/L was prepared and called "Culture Solution I".

To the Culture Solution H, a 2 mol/L aqueous lysine hydrochloride solution was further added, whereby a culture solution containing lysine at a final concentration of 0.1 mol/L was prepared and called "Culture Solution J". To the Culture Solution H, a 0.75 mol/L aqueous histidine hydrochloride solution was further added, whereby a culture solution containing histidine at a final concentration of 0.1 mol/L was prepared and called "Culture Solution K".

Each of thus prepared culture solutions was centrifuged at 2090×g for 10 minutes to precipitate the cells, large cell fragments, and the like, and the culture supernatant was recovered. Subsequently, by filtering each of the culture supernatants using Millex-GP (Product No. SLGP033RS, manufactured by Millipore, Inc.), the membrane filterability of the respective culture supernatants was evaluated. Incidentally, this membrane filterability replicated the membrane filterability in the cell separation step.

As a result, the culture supernatants derived from the Culture Solutions A, B, C, D, E, F, G, H, I, J, and K caused clogging of the membrane at the time when being filtered through the membrane in an amount of about 16.2 mL, 17.5 mL, 18.1 mL, 18.4 mL, 24.9 mL, 23.0 mL, 22.2 mL, 26.8 mL, 27.3 mL, 26.8 mL and 28.2 mL, respectively.

Based on the results of the Culture Solutions A, B, C and D, it was revealed that the membrane filterability in the cell separation step is not decreased by the addition of arginine, lysine, or histidine to the culture solution. Further, based on the results of the Culture Solutions H, I, J, and K, it was revealed that the membrane filterability in the cell separation step is not decreased by the addition of arginine, lysine, or histidine to the culture solution after performing acid precipitation.

Still further, based on the results of the Culture Solutions B, C, and D, Culture Solutions E, F, and G, and Culture Solutions I, J, and K, it was revealed that the membrane filterability in the cell separation step is improved by the addition of arginine, lysine, or histidine to the culture solution either before or after performing acid precipitation as compared with the case where acid precipitation is not performed. However, it was revealed that the addition of arginine, lysine, or histidine to the culture solution may be performed before performing acid precipitation, but more preferably, it is performed after performing acid precipitation.

While the invention has been described in detail and with reference to specific embodiments thereof, it will be apparent to one skill in the art that various changes and modifications can be made therein without departing from the spirit and scope thereof. This application is based on U.S. provisional application No. 61/709,311, filed on Oct. 3, 2012, the entire contents of which are incorporated hereinto by reference.

The invention claimed is:

1. A method for purifying a polypeptide from a culture solution containing the polypeptide and a recombinant host cell which is capable of producing the polypeptide, said method comprising the following steps:
   (a) a flocculation step, wherein the flocculation step comprises acid precipitation of the culture solution;
   (b) centrifuging the culture solution of step (a) to recover a culture supernatant;
   (c) filtering the culture supernatant; and
   (d) isolating the polypeptide from the filtrate obtained from step (c),
   wherein the method further comprises adding arginine to the culture solution either before or after step (a).

2. The method according to claim 1, wherein the polypeptide is an antibody or an antibody fragment.

3. The method according to claim 1, wherein the recombinant host cells are Chinese hamster ovary (CHO) cells.

4. The method according to claim 1, wherein the arginine is added to the culture solution before step (a).

5. The method according to claim 1, wherein the arginine is added to the culture solution after step (a).

6. The method according to claim 5, wherein the arginine is added to the culture solution so that the final concentration of the arginine is from 0.05 mol/L to 1 mol/L.

7. The method according to claim 5, wherein the arginine is added to the culture solution so that the final concentration of the arginine is 0.5 mol/L.

8. The method according to claim 5, wherein the arginine is added to the culture solution so that the final concentration of the arginine is 0.1 mol/L.

9. The method according to claim 5, further comprising adding arginine to the culture solution after step (c).

10. The method according to claim 5, wherein arginine is added to the culture solution after step (a), and before step (b).

* * * * *